United States Patent [19]

Auvil et al.

[11] 4,272,452

[45] Jun. 9, 1981

[54] PROCESS FOR PREPARING ACETONITRILE

[75] Inventors: Steven R. Auvil, St. Louis; Charles R. Penquite, Ballwin, both of Mo.

[73] Assignee: Monsanto Company, St. Louis, Mo.

[21] Appl. No.: 106,775

[22] Filed: Dec. 26, 1979

[51] Int. Cl.³ .................. C07C 120/00; C07C 121/18
[52] U.S. Cl. .................................. 260/465.1; 423/376
[58] Field of Search ...................................... 260/465.1

[56] References Cited

U.S. PATENT DOCUMENTS 4,179,462  12/1979  Olivé et al. .................. 260/465.9 X

*Primary Examiner*—Joseph Paul Brust
*Attorney, Agent, or Firm*—Joseph D. Kennedy; James W. Williams, Jr.

[57] ABSTRACT

A process for preparing acetonitrile by reaction of carbon monoxide, ammonia and hydrogen at elevated temperature in contact with metal-containing catalysts, in which carbon dioxide is utilized to improve selectivity to acetonitrile. At elevated pressure, more than 2 moles carbon dioxide per mole carbon monoxide can be used effectively.

15 Claims, 1 Drawing Figure

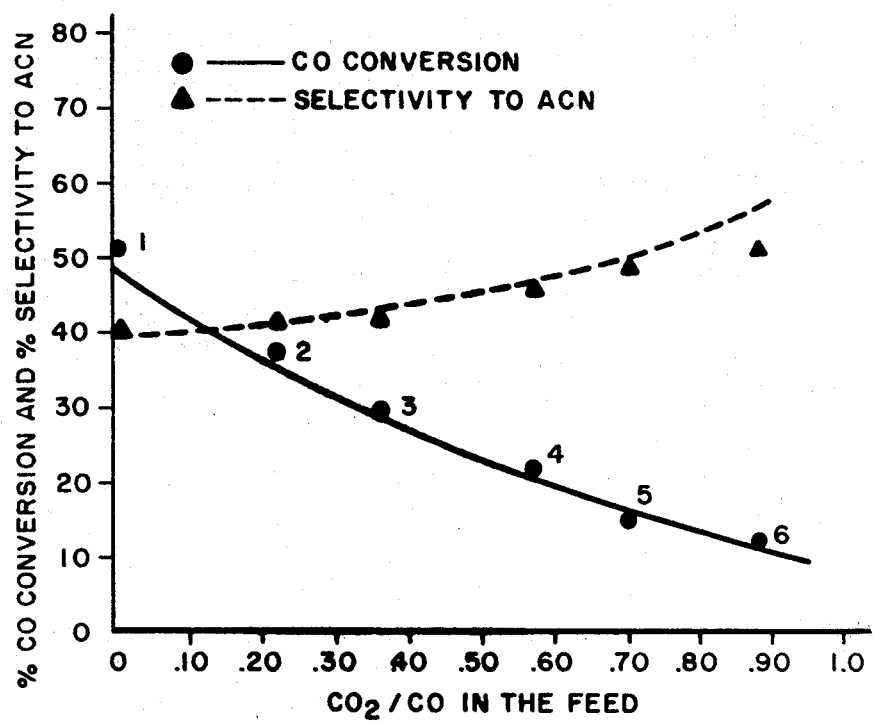

PROCESS FOR PREPARING ACETONITRILE

The present invention concerns an improvement in a process for preparing acetonitrile from the reaction of carbon monoxide, hydrogen and ammonia. In particular, the invention involves the use of carbon dioxide in the process in order to improve selectivity to acetonitrile.

BACKGROUND OF THE INVENTION

A commonly assigned patent of G. and S. Olivé, U.S. Pat. No. 4,179,462, issued Dec. 18, 1979, describes a process in which acetonitrile is prepared by high temperature reaction of carbon monoxide, hydrogen and ammonia over a transition metal catalyst. Various catalysts and operating conditions are exemplified.

It happens that the described reaction is usually accompanied by a number of side reactions, with the significance of particular reactions depending upon the catalyst and other conditions.

SUMMARY OF THE INVENTION

The present invention involves the use of carbon dioxide in the production of acetonitrile from carbon monoxide, ammonia and hydrogen in order to improve selectivity to acetonitrile. The reaction is conducted at elevated temperature over an effective catalyst. Small amounts of carbon dioxide have some effect, but the most useful amounts will be in the range of greater than about 0.5 mole or often greater than 1 or so moles $CO_2$ for each mole CO, on up to possibly 5 or so moles $CO_2$ per mole CO. The selectivity to acetonitrile increases with increasing amounts of $CO_2$, but there is also a continuing decline in conversion in the process which tends to limit the advantage of higher amounts of $CO_2$, and it is also undesirable to have unnecessarily excessive volumes of components for handling. There is an advantage to operation at elevated pressures in order to increase reactor volumetric production, through-put, particularly because of the large volumes resulting from use of $CO_2$, and the low conversions with the necessary recycling.

A particular aspect of the invention involves use of fairly high amounts of carbon dioxide in conjunction with elevated pressure. When carbon dioxide is employed in the process, higher pressures shift the equilibrium and make it possible to push the process to higher conversions, thereby making a better combination of conversion and selectivity to acetonitrile possible. Thus the process will generally be operated at at least 100 psi gauge, and more likely over 300 or 500 psi gauge to obtain suitable conversions when amounts of carbon dioxide in excess of 1 mole per mole carbon monoxide are used.

In a particular aspect, the invention involves using and maintaining carbon dioxide in the feed stream so that conversions are no greater than 10 to 30 percent or so, separating product, and recycling unreacted components and carbon dioxide with additional reactant feed.

DETAILED DESCRIPTION OF THE INVENTION

The present process can utilize the general procedures and catalysts described in the aforesaid U.S. Pat. No. 4,179,462. In general the present process can utilize any catalyst effective for the reaction and sufficiently elevated temperatures, such as in excess of 350° up to about 600° C. With some of the more suitable catalysts, the temperatures will be in excess of 450° or 500° C. for good activity. However any elevated temperature effective for producing acetonitrile with a particular catalyst can be employed. The aforesaid application describes transition metal catalysts in a reduced valence state, and such catalysts can be employed in the present invention. Moreover catalysts in addition to those exemplified there can be employed in the present invention if effective for producing acetonitrile. It appears that in general conditions which favor production of acetonitrile, also cause the water gas shift reaction. A number of metal and metal oxide catalysts are known as water gas shift catalysts and the present invention will be useful when any of these are utilized or are present in a process for producing acetonitrile from the described reactants.

The production of acetonitrile can be represented:

$$2CO + 2H_2 + NH_3 \rightleftharpoons 2H_2O + CH_3CN \qquad (1)$$

However the reaction is equilibrium limited under usual conditions, as well as accompanied by a number of side reactions as described hereinbelow.

While we do not wish to be limited to any particular theory or mechanism, it appears that a significant factor in the improved selectivity is a lower loss of carbon dioxide to other reactions such as the water gas shift reaction. The water gas shift reaction is:

$$CO + H_2O \rightleftharpoons H_2 + CO_2 \qquad (2)$$

The water gas reaction utilizes water from reaction (1) above, and may cause a large loss of carbon monoxide reactant. While the use of carbon dioxide improves selectivity to acetonitrile, it also affects the conversions available.

A choice can be made as to the appropriate balance of conversion and selectivity, and the amount of carbon dioxide and other conditions selected accordingly. With appropriate conditions and catalyst, the addition of carbon dioxide makes it possible to raise the selectivity to acetonitrile based on carbon monoxide, from less than 40% to over 80%. This increase in selectivity is accompanied by a decline in conversion, such as from a value around 60% to a value less than 20%, or lower, depending upon conditions. While the low conversions are a disadvantage, the higher selectivity may make the actual yield of acetonitrile per pass through the catalyst approximate that from higher conversions, and with much less use of carbon monoxide reactant. The residual carbon monoxide can then be recycled to produce additional acetonitrile.

The amounts of carbon dioxide can be varied, but ordinarily at least 0.5 mole per mole of carbon monoxide will be used, and probably in excess of 1 mole per mole of carbon monoxide up to 5 or so moles per mole carbon monoxide. The conversions obtainable vary in inverse manner with the amount of carbon dioxide. Under ambient pressure, or mild pressures up to about 100 psi gauge, it is feasible to achieve selectivity to acetonitrile around 55 to 60% at conversions of 5 to 10% or so. Because of declining conversions, there is not much advantage in using carbon dioxide at much more than a mole to mole ratio with carbon monoxide at such mild pressures. However, if the pressure is increased to the range of about 500 to 1000 psi gauge or more, larger amounts of carbon dioxide are advantageous and selectivities of 80% or more are obtainable at conversions around 15%. Such processes may involve carbon dioxide to carbon monoxide mole ratios of 1.5:1 up to 4:1 or higher. Of course, reaction time, as measured by space velocity, also affects conversion, but the process will generally be conducted so that conditions approach equilibrium, employing space velocity to have the selectivity approach the maximum obtainable under the conditions utilized, and accepting the conversions obtainable or obtaining the best conversions feasible without marked loss of selectivity. While economic as well as other considerations will be involved in a determination of the most appropriate conditions from a practical standpoint, such conditions will usually involve accepting conversions in the range of about 10% to about 30 or 40%, more likely in the range of about 15% to about 30%. The space velocity to obtain such conversions will vary with temperature, pressure, catalyst and other conditions, but will usually be in the range of about 200 to about 4000 reciprocal hours (at standard temperature and pressure). The use of high pressure and large volumes of carbon dioxide has some effect on catalyst activity, necessitating use of lower space velocity to obtain conversions comparable to those otherwise obtainable at higher space velocities. In some cases operation at faster or slower space velocities than usual may be appropriate, e.g. from about 50 to about 5000 reciprocal hours. The space velocity as used herein means the volume of gases, with reference to standard temperature and pressure, charged per hour to unit volume of catalyst, and can be designated in reciprocal hours, or gaseous hourly space velocity (GHSV).

Since the use of elevated pressure and fairly high volumes of carbon dioxide results in a better combination of conversion and selectivity to acetonitrile, operation from a practical and economic standpoint will ordinarily involve such conditions. The process is preferably operated at at least about 300 psi gauge up to 1000 or so psi gauge and at temperatures of about 450° C. to 550° C. and employing $CO_2$:CO in a mole ratio above about 1.5:1 and usually in excess of about 2:1. The ratio of the reactants can vary widely, but either excessive hydrogen or insufficient ammonia tends to increase the production of hydrocarbon at the expense of nitrile. Therefore it is desirable to utilize the reactants in CO:$NH_3$:$H_2$ mole ratios in the range of 1:1.5–3.5:0.1–1 to favor the production of acetonitrile. There is generally advantage in not having the hydrogen in excess of the carbon monoxide. However, some of the benefits of the present invention can be obtained over broader ranges, such as CO:$NH_3$:$H_2$ mole ratios of 1:1–4.5:0.1–2. When the process is conducted under pressure, the desired ratios of the reactants will determine the partial pressures of each contributing to the total pressure. If, desired, diluent gases can be present. At equivalent space velocities with such diluents present, there is an increase in HCN production at the expense of acetonitrile production. If diluents are employed in the process, adjustment for optimum operation can be made, utilizing the exemplifications illustrated herein. However in practice there will be large volumes of gases to handle and recycle because of the use of the carbon dioxide, together with the generally low conversions in the process. Ordinarily the presence of additional volumes of diluents will be undesirable. Preferred catalysts in the present process can be chosen on the basis of activity for the desired reaction with minimum activity for undesirable reactions. Included in a list of reactions which are undesirable is the afore-mentioned water gas shift reaction, and carbon monoxide disproportionation.

$$2CO = C + CO_2 \tag{3}$$

Other side reactions include:
Ammonia dissociation $$2NH_2 = N_2 + 3H_2 \tag{4}$$

Other carbon containing products
hydrocarbons, olefins/paraffins $$e.g., CO + 3H_2 = CH_4 + H_2O \tag{5}$$

and higher homologues,
amines, $$e.g. CO + 2H_2 + NH_3 = CH_3NH_2 + H_2) \tag{6}$$

and higher homologues,
other nitriles, $$CO + NH_3 = HCN + H_2O \tag{7}$$

and higher homologues,
Reactions with catalysts, $$e.g., 6CO + 2MoO_2 = Mo_2C + 5CO_2 \tag{8}$$

It will be desirable to maximize the formation of acetonitrile while minimizing side reactions such as reactions 3–8 above. In part, this is influenced by reaction conditions and conditions for obtaining good acetonitrile selectivity are illustrated herein. In addition, certain catalyst types catalyze the side reactions to much lower extents than others.

Under normally employed reaction conditions, the levels of HCN, acetonitrile, and $CO_2$ (via the water gas shift reaction) observed in the reaction products are at or near levels in accord with thermodynamic calculations. However, the observed levels of the other products defined by the above reactions (3)–(8), are well below the levels arrived at by thermodynamic calculations; i.e., the kinetic rates of these reactions are strongly limited by the catalysts employed.

Despite theory concerning the effect of addition of a product material to an idealized reacting system at chemical equilibrium in causing a decline in net formation of the product, to a degree depending upon thermodynamic relationships, in practice it is seldom possible to predict the effect that adding an excess of one or more products to the reaction feed will have on the product distribution in a catalyzed reaction system; this is especially true when a few reactions are under equilibrium control and the remaining reactions are under kinetic control. The potential interactions the added material can have with the catalyst and/or other reactants and products are endless as are the effects that these interactions have on the kinetics of all of the reactions occurring in the system.

We have found, to our surprise, that adding $CO_2$ to the feed gases does not, to any appeciable degree, harm the performance of catalysts which selectively cause the formation of acetonitrile from CO, $H_2$, and $NH_3$. In fact, the selectivity to acetonitrile is enhanced by more than would be expected by simply reducing the formation of $CO_2$ formed by the water gas shift reaction. The formation of higher nitrile homologues than acetonitrile is essentially eliminated, no amines are observed, and the formation of hydrocarbons other than methane are greatly reduced. Methane formation is reduced slightly. The formation of HCN and acetonitrile is maintained at equilibrium levels by lowering the total feed gas to catalyst ratio slightly relative to the case in which $CO_2$ is not added to the feed.

The carbon dioxide is employed in the present process in part to inhibit the water gas shift reaction, but it is not necessary to suppress it completely, and conversions would generally be fairly low under such conditions. However, it is possible to have virtually complete suppression or to keep conversion to $CO_2$ to less than 10%, and very good selectivity to acetonitrile can be obtained by such procedure. There will generally be no advantage in using such high amounts of carbon dioxide as to drive the water gas shift reaction in the reverse direction, i.e., to have a net conversion of carbon dioxide to carbon monoxide. Use of relatively low amounts of hydrogen also mitigates against this reverse reaction.

Since a factor in the effectiveness of the presently described invention is due to equilibrium considerations, it has general application to catalytic processes for preparing acetonitrile from the described reactants. The inhibition of the water gas shift reaction can be expected to enhance selectivity to acetonitrile, aside from the particular catalyst involved; therefore the invention is useful with a variety of catalysts. However, there is a wide variation in the selectivity to acetonitrile obtainable with various catalysts, and it will generally be desirable to employ the more effective catalysts in the present invention.

Improved catalysts for the synthesis of acetonitrile from synthesis gas plus ammonia are described in copending application Ser. No. 106,776 filed Dec. 26, 1979, by James W. Gambell and Steven R. Auvil. Molybdenum-containing catalysts, modified with alkaline earths or manganese, have been found to be among the most suitable. However, catalysts based on actives other than molybdenum and optionally containing modifiers may be found capable of achieving selectivities to acetonitrile upwards of 50 to 75% and therefore can be among preferred catalysts for the process of the present invention. A number of effective catalysts involve actives chosen from the B-subgroups of Groups V, VI, VII of the Periodic Table of the Elements. Members of Group VIII can be effective also. For example, iron has good activity for the desired reaction, but also strongly catalyzes disproportionation of carbon monoxide, limiting its value, in unmodified forms, in the present process. Transition metals in reduced valence state constitute a group of catalysts which are generally effective, although there is variance in the degree of effectiveness.

We have found that superior catalysts for the desired reaction, with minimum by-product formation, can be selected from V, Mo, W, and Re. The actives may be used in unsupported form, or alternatively employ a support selected from activated alumina, silica gel, diatomaceous earth, thoria, ceria, silica alumina, and pumice, or generally any of the common refractory catalyst supports. From a practical standpoint there may be advantage in use of supports with respect to long term stability and retention of activity. Among the effective catalysts particularly suited for the present process are molybdenum containing preparations modified with alkaline earths or with manganese and optionally containing potassium. Such catalysts can be employed in unsupported form or with supports. The amounts of each additive will depend on the presence or absence of supports. Unsupported preparations may be used in stoichiometric ratios, $MnMoO_4$, $MgMoO_4$, or $SrMoO_4$ written in oxidized form. With supported catalysts the appropriate amount of each additive will depend on the nature of the support. With supports which do not interact strongly with molybdenum, such as silica gel, loadings of molybdenum on the order of 10% (by weight as molybdenum metal) are very effective. On the other hand, with supports which interact more strongly with molybdenum such as activated alumina, higher molybdenum loadings will be required; for example, loadings of molybdenum as high as 20% or even higher may be advisable for best results. It is understood that the molybdenum loading employed will depend, in part, on the surface area of the support, with higher surface areas calling for higher loadings. Illustrative loadings specified for silica gel and for activated alumina are appropriate for support materials with surface areas on the order of 300 and 300 $m^2/g$ respectively. While broad ranges of molybdenum can be employed, e.g. from 1% or preferably from 5% up to 20–30% or more by weight, there is advantage in selecting loadings for particular supports as indicated. Likewise, the preferred amount of alkaline earth and/or manganese to employ with molybdenum will depend on the support chosen. With weakly interacting supports the ratio (molar) of additive to molybdenum can be about 1:1 and give good results. With strongly interacting supports, the ratio will generally depend on molybdenum loadings the lower the molybdenum loading the higher the ratio required. Thus, while 1:1 ratios may give good results at higher molybdenum loadings (on the order of 20% Mo calculated at $MoO_3$) at lower loadings more alkaline earth and/or manganese will be required for optimum catalyst performance. Thus, with activated alumina supports and molybdenum loadings of 10%, w/w, ratios of 1.5:1 or higher may be desirable.

The catalysts utilized herein can be prepared by a variety of means, for example in accord with procedures described in the aforesaid Ser. No. 4,179,462. For example, water soluble salts of selected additives, e.g. molybdenum and manganese, or molybdenum and strontium, and optionally potassium, may be impregnated on a catalyst support and subjected to oxidizing conditions followed by reducing conditions.

Water soluble salts or complexes can be used in preparing the catalysts used in the present invention. For example, vanadyl oxylate complexes, ammonium para molybdate, meta-tungstic acid, ammonium perrhenate, and nitrates of alkaline earths, manganese and potassium have been employed. Other salts, or other methods of preparation will generally suffice to produce active catalysts for the present invention. Removal of the majority of water after impregnation can be accomplished by drying at about 100° C. Depending on the particular catalyst preparation in question, an oxidation treatment to convert the impregnated salt to an oxidized form of the metal(s) in question can be employed advantageously. The oxidation can be performed conveniently in air. The temperature of oxidation will, of course, depend on the additives present and also the presence of particular supports. For example, temperatures high enough to cause sublimation of molybdenum or tungsten are to be avoided. Also, temperatures high enough to cause adverse effects on support properties likewise should be avoided; e.g.. with V, Mo, W additives, calcination temperatures wil generally be low enough when activated alumina is employed as support to avoid conversion of support to alpha alumina.

Catalysts employed in the present invention are generally employed in reduced form. This does not necessarily imply reduction to the metal. Rather, the oxidized catalyst form can be activated by treatment with hydrogen at elevated temperature, such as 500° C. With the possible exception of Re, intermediate average valence between that of metal and of fully oxidized catalyst will be obtained. In the case of thorium and cerium only a small degree of reduction is accomplished. Moreover, as the conditions for acetonitrile production are reducing, involving carbon monoxide, hydrogen and ammonia at elevated temperatures, catalysts employed with present invention can be activated in situ by being subjected to appropriate reaction conditions in the presence of reactants.

The reaction is suitably carried out by conducting the reactants over the catalyst at elevated temperature with a residence time sufficient to effect the reaction. The reaction can conveniently be carried out for demonstration purposes utilizing a glass (high temperature) reactor tube with capacity for about 10 cm$^3$ of catalyst packed into the tube and held with quartz wool plugs.

As a normal charge, about 5 cm$^3$ (bed depth about 2.5 cm) catalyst is employed. A glass thermowell extends along the central axis of the reactor tube, through the catalyst bed, permitting temperature measurement by suitably positioning a thermocouple. The tube is contained within a metal shell to permit safe operations at elevated pressure, and placed within a radiantly heated furnace, and provided with temperature controls and means for preheating the feed gas. The components of the feed gas are mixed prior to entering the reactor, and on-line gas chromatographs are available for measuring the feed and product streams. The described apparatus is suitable for use at moderately elevated pressures. Modifications can be made for operations at higher pressures, or types of equipment generally employed for high pressure operations can be used. In general it is desirable to employ glass or other refractory materials as components or liner materials in reactant zones to avoid possible effects of metal contact upon the reactant gases. The reactor as described can be used but with a steel container with a glass liner for the reaction zone. A gold coating on the steel has been found effective in limiting possible effects of contact of the gases with the metal.

EXAMPLE 1

Employing a reactor tube as described above, carbon monoxide, ammonia and hydrogen were conducted over a modified molybdenum catalyst at temperature of 500° C. and pressure of 100 psi gauge to produce acetonitrile. The reactants in the feed stream were employed in ratios on a molecular basis, $CO:NH_3:H_2$ of 1:1.92:0.37. Varying amounts of carbon dioxide were added to the feed, as reported below

| Run | $CO_2/CO$ Mole ratio | GHSV (STP) | % CO Conversion | Selectivity to ACN |
|---|---|---|---|---|
| 1 | 0 | 1305 | 48 | 39.7 |
| 2 | .22 | 1390 | 37.5 | 41.6 |
| 3 | .36 | 1445 | 29.5 | 42.4 |
| 4 | .57 | 1530 | 21.5 | 46.8 |
| 5 | .7 | 1580 | 15.5 | 49.3 |
| 6 | .88 | 1655 | 12.5 | 51.2 |

The catalyst utilized was a molybdenum on alumina catalyst which also contained manganese, with 8.9% molybdenum and 5.1% manganese, the percentage being by weight.

It can be seen from the results above that selectivity to acetonitrile is improved and increases with increasing amounts of carbon dioxide. However the conversion declines as the amount of carbon dioxide increases. The carbon monoxide conversion and acetonitrile selectivity values approximate equilibrium values calculated from thermodynamics, after experimental conclusions concerning the characteristics of the reactions involved.

The results from above are graphically illustrated in the FIGURE in which the points are the experimental values while the lines are theoretical values.

The catalyst utilized in Example 1 was prepared as follows. A 5×8 mesh gel derived alumina support (kaiser B$_r$-2025) with low $Na_2O$ content was calcined 5 hours at 600° C. in air. Utilizing minimum solution technique, a 20 gram amount of the support was impregnated with ammonium paramolybdate (($NH_4)_6Mo_7O_{24}.4H_2O$, powder), 4.09 grams, dissolved in 14.1 ml water (10% excess water). The material was then air dried at 120° C. for 3 hours and calcined for 3 hours at 600° C. The calcined material was then impregnated with 14.1 ml aqueous solution containing 8.28 grams of $Mn(NO_3)_2$ (diluted with water from 50% by weight aqueous solution). The material was then air dried at 120° C. for 3 hours and calcined for 3 hours at 600° C. The impregnation with $Mn(NO_3)_2$, drying and calcination was then repeated. (The double impregnation was used because of the dilute $Mn(NO_3)_2$ used). The catalyst was used directly in the above acetonitrile preparation. The catalyst had 8.9 weight percent Mo and 5.1 weight percent Mn on alumina, surface area of 148 m$^2$/gm. A uniform pretreatment of the catalyst in the reactor was employed, involving heating to 200° C. under nitrogen, gradually heating to 500° C. under 44% hydrogen in nitrogen, and then holding about 12 hours under hydrogen.

EXAMPLE 2

Using a reactor of the type described herein, adapted for use at pressures up to 1000 psi gauge, it was found that increased pressure improved the conversions obtainable in the presence of relatively high amounts of carbon dioxide. The data presented in Table I were obtained employing an unsupported magensium molybdate catalyst operating at 500 psi (gauge) and 500° C. The $CO_2:CO$ molar feed ratio was varied from run to run while the $CO:NH_3:H_2$ molar feed ratio was held constant at 1:2.94:0.27 in all runs. In order to keep the reactor running as near to equilibrium as possible the gas hourly space velocity (STP) was reduced as increased amounts of $CO_2$ were added to the feed.

The results in Table I show clearly the beneficial influence of $CO_2$ addition to the feed gases. Without $CO_2$ addition, Run No. 1, only 37.9% of the CO converted results in acetonitrile formation with 45.8% of the CO converted lost to $CO_2$. However, adding 2.74 moles of $CO_2$ per mole of CO in the feed, Run No. 5, increases the CO selectivity to acetonitrile to 79.7% with essentially no CO loss to $CO_2$.

TABLE I

Improved Carbon Monoxide Selectivities To
Acetonitrile With Various Amounts of Carbon
Dioxide Added To The Feed.
Catalyst: Unsupported Magnesium Molybdate
Temperature: 500° C.
Pressure: 500 psi (gauge)
CO:NH₃:H₂ molar feed ratio: 1:2.94:0.27

| Run No. | CO$_2$:CO mole ratio | GHSV @STB | % CO Converted | % Selectivity | | | | Sel. Ratio (Acetonitrile Other* Products) |
|---|---|---|---|---|---|---|---|---|
| | | | | ACN | CO$_2$ | HCN | Other Products Total* (by difference) | |
| 1 | 0 | 8040 | 61.8 | 37.9 | 45.8 | 3.0 | 16.3 | 2.33 |
| 2 | 1.96 | 3970 | 17.0 | 58.4 | 23.3 | 11.8 | 18.3 | 3.19 |
| 3 | 2.21 | 4000 | 14.7 | 59.9 | 18.0 | 14.1 | 22.1 | 2.71 |
| 4 | 2.50 | 2500 | 17.0 | 66.7 | 16.0 | 8.3 | 17.3 | 3.86 |
| 5 | 2.74 | 2600 | 13.7 | 79.7 | 0 | 11.5 | 20.3 | 3.92 |

*In addition to HCN, includes methane and propionitrile - small amounts of C$_2$ and C$_3$ hydrocarbons were also observed in Run #1.

From the Selectivity Ratio values in Table I it can be seen that with CO$_2$ addition and decline in CO$_2$ production, the selectivity to acetonitrile was enhanced not only with respect to carbon dioxide but at the expense of other products as well. In addition, the HCN produced is not a loss, as it results from an equilibrium reaction, and can be recycled to prevent its further production in subsequent cycles. Thus the actual improvement at the expense of concomitant products is much greater than that illustrated by the Selectivity Ratio results. (The Selectivity Ratio is the ratio of the selectivity to acetonitrile to the selectivity to other products).

The magnesium molybdate catalyst utilized above was prepared by tableting magnesium molybdate power, without binding agents or lubricants, directly in a pellet press. The resulting pellets were right cylinders, nominally ⅛ inch diameter and ¼ inch length. The pellets were broken into 10×20 mesh particles for use, and used directly, being activated to the extend needed by conditions in the reactor. The catalyst is designated as unsupported magnesium molybdate, MgMoO$_4$, with such reduction as occurs in use. Magnesium molybdate utilized for the catalyst was obtained from Climax, Molybdenum Company, 1270 Avenue of the Americas, New York, N.Y. 10020. The material can be prepared by reacting magnesium chloride, MgCl$_2$, with silver molybdate, Ag$_2$MoO$_4$, in aqueous solution in accord with a procedure described in "The System Magnesium Molybdate-Water and the 25° C. Isotherm of the System MgMoO$_4$-MgCl$_2$-H$_2$O", by John E. Ricci and William F. Linke, J. Am. Chem. Soc. 73,3603, (1951).

EXAMPLE 3

Using a reactor of the type described herein, adapted for use at pressures up to 1000 psi gauge, it was found that increased pressure improved the conversions obtainable in the presence of relatively high amounts of carbon dioxide. From data obtained employing a molybdenum catalyst modified with strontium, the following is postulated as illustrative of good operating conditions and results. A reactor feed is employed with CO:NH$_3$:H$_2$:CO$_2$ in mole ratios of 1:2:0.5:2.3, at a space velocity (STP) of 500 reciprocal hours, and temperature of 500° C. at 815 psi (gauge). From this a 19% conversion of carbon monoxide is expected, with a selectivity to acetonitrile of 81% based on carbon monoxide. While of less interest to the present process, the selectivities based on ammonia and hydrogen are projected as 91% and 78% respectively. The strontium catalyst utilized for obtaining data was prepared as follows. As support 1/16 inch extruded alumina (Linde, type 60-503) with low iron content was utilized. The support was calcined 5 hours at 600° C. in air prior to use, and had 215 m$^2$/gram surface area. In order to obtain the desired molybdenum loading, successive impregnations were made involving impregnation of 25 grams of the support with 4.71 gram ammonium paramolybdate powder dissolved in 20.6 cc water, followed by air drying at 120° C. for 2 hours, and calcining for three hours at 500° C., and then repetition of the impregnation, drying and calcining steps. The molybdenum impregnated alumina was then impregnated with strontium nitrate, employing 5.56 grams strontium nitrate in 8 ml water for 12.72 grams of the molybdenum impregnated alumina. The material was then air dried at 120° C. for 2 hours and calcined in a muffle furnace for 5 hours at 600° C. The resulting material contained 13 weight percent Mo and 14.6 weight percent Sr (both metal basis) on alumina, and was used directly in reactions as described herein.

What is claimed is:

1. In a process for producing acetonitrile by reaction of carbon monoxide, ammonia and hydrogen at elevated temperature in excess of 350° C. and pressures in excess of 100 psi gauge in contact with a catalyst for such reaction, which is a transition metal in reduced valence state, the improvement which comprises utilizing feed gas with operative ratios of such reactants in CO:NH$_3$:H$_2$ mole ratios of 1:1-4.5:0.1-2 and providing carbon dioxide in the feed gas to improve selectivity of the conversion of carbon monoxide to acetonitrile and in amount at least about 0.5 mole per mole of carbon monoxide and sufficient to retard substantially the conversion of carbon monoxide, and obtaining acetonitrile with improved selectivity.

2. The process of claim 1 in which carbon monoxide is utilized in an amount at least equimolar with hydrogen.

3. The process of claim 1 in which the amount of carbon dioxide is in the range of about 0.5 mole of 5 moles per mole of carbon monoxide.

4. The process of claim 1 in which the reaction is run at time, temperature and pressure conditions such that the conversion based on carbon monoxide is no greater than 30%.

5. The process of claim 1 in which the amount of carbon dioxide is at least about 1 mole per mole of carbon monoxide.

6. The process of claim 1 in which the reaction is conducted with a $CO_2$:CO ratio of at least 1.5.

7. The process of claim 6 in which the temperature is in the range of 450° to 550° C., pressures in the range of about 300 to about 1000 psi gauge and $CO_2$:CO ratio in the range of 1.5:1 to 4:1 with CO at least equimolar to hydrogen and a space velocity is utilized such that the conversion is in the range of about 10 to about 30% based on carbon monoxide.

8. The process of claim 7 in which a molybdenum catalyst is employed with selectivity to acetonitrile in excess of 60%.

9. The process of claim 1 in which reactants are removed from the reaction zone after a conversion substantially less than the optimum conversion obtainable under the reaction conditions but in the absence of carbon dioxide.

10. The process of claim 1 in which the catalyst is a transition metal catalyst is reduced valence state.

11. The process of claim 1 in which the catalyst comprises metal selected from vanadium, molybdenum, tungsten and rhenium.

12. The process of claim 1 in which the catalyst comprises molybdenum.

13. The process of claim 1 in which the catalyst is a strontium modified molybdenum catalyst.

14. The process of claim 1 in which the catalyst is a manganese modified molybdenum catalyst.

15. The process of claim 1 in which the amount of $CO_2$ is such as to keep conversion of CO to $CO_2$ to less than 10%.

* * * * *